United States Patent
Jost et al.

[11] Patent Number: 5,925,783
[45] Date of Patent: Jul. 20, 1999

[54] PROCESS FOR THE PREPARATION OF ISOCYANATES

[75] Inventors: Klaus Jost, Dormagen; Günter Hammen, Rommerskirchen; Rudolf Sundermann, Leverkusen, all of Germany

[73] Assignee: Bayer Aktiengesellschaft, Leverkusen, Germany

[21] Appl. No.: 08/836,294

[22] PCT Filed: Nov. 6, 1995

[86] PCT No.: PCT/EP95/04354

§ 371 Date: May 12, 1997

§ 102(e) Date: May 12, 1997

[87] PCT Pub. No.: WO96/16028

PCT Pub. Date: May 30, 1996

[30] Foreign Application Priority Data

Nov. 17, 1994 [DE] Germany .............................. 44 40 917
Jun. 16, 1995 [DE] Germany .......................... 195 21 800

[51] Int. Cl.$^6$ ................................................ C07C 263/00
[52] U.S. Cl. ............................................... 560/347
[58] Field of Search ............................................ 560/347

[56] References Cited

U.S. PATENT DOCUMENTS

| | | | |
|---|---|---|---|
| 2,822,373 | 2/1958 | Beck | 260/453 |
| 3,287,387 | 11/1966 | Denton et al. | 260/453 |
| 3,781,320 | 12/1973 | Irwin | 260/453 PH |
| 3,978,105 | 8/1976 | Fuchs et al. | 260/453 PH |
| 4,422,976 | 12/1983 | Yamamoto et al. | 260/453 PH |

FOREIGN PATENT DOCUMENTS

| | | |
|---|---|---|
| 1191641 | 5/1965 | Germany . |
| 60-10774 | 1/1985 | Japan . |
| 1255638 | 12/1971 | United Kingdom . |
| 1341311 | 12/1973 | United Kingdom . |

*Primary Examiner*—Samuel Barts
*Attorney, Agent, or Firm*—Joseph C. Gil; Lyndanne M. Whalen

[57] ABSTRACT

Isocyanates are prepared by a continuous process by reacting appropriate primary amines with phosgene in the presence of an isocyanate as solvent, the primary amine optionally dissolved in an inert organic solvent being reacted with phosgene, which is dissolved in the isocyanate, at temperatures of 60 to 150° C. and at pressures of 1 to 30 bar ($10^5$ to $3.10^6$ Pa) to obtain the corresponding isocyanate, wherein the molar ratio of phosgene to amine used is 4:1 to 1:1, and the isocyanate used as solvent is solids-free and has a value for hydrolysable chlorine of less than 2%.

4 Claims, No Drawings

PROCESS FOR THE PREPARATION OF ISOCYANATES

This application is a 371 of PCT/EP95/04354 filed Nov. 6, 1995.

The present invention relates to a process for the preparation of organic isocyanates by reacting the appropriate amines with phosgene.

During the preparation of organic isocyanates, the appropriate amine is reacted with phosgene, the organic isocyanate being formed with hydrogen chloride as by-product. As a rule, an excess of phosgene is used, with the result that the gas obtained as a by-product is a mixture of hydrogen chloride and phosgene.

Various methods for carrying out said process are already described in the literature. Even slight economic improvements in such an important industrial-scale process are evidently of great economic interest.

Many of the known processes have disadvantages such that, for example, they achieve high yields only if the concentrations of the reactants are kept at a low level, or they require long reaction and residence times.

It is well known to prepare organic isocyanates in two stages by reacting primary amines with an excess of phosgene at temperatures up to approx. 80° C. and then subjecting the product containing carbamoyl chloride to a further treatment with phosgene at higher temperatures to form the corresponding isocyanate. On an industrial scale, the reaction of amines with phosgene is usually carried out in phosgenation towers (at atmospheric pressure or under a moderate pressure).

It is also well known (U.S. Pat. No. 28 22 373) to prepare organic isocyanates continuously by mixing a phosgene solution in a turbulent flow with a solution of an organic amine in a reactor which is operated in a closed circuit. In said process, the solution of the isocyanate in the organic solvent may be returned to the reactor in a closed circuit in order to increase the concentration of isocyanate in the solution. A disadvantage of said process is that the maximum concentration of the isocyanate in the circuit should not be substantially above 15% and the concentration of the organic amine in the solvent should be only 5 to 30%.

In DE-A 18 11 609, solutions of isocyanate in an organic solvent are recycled during phosgenation in the presence of an at least 400% excess of phosgene.

Other phosgenation reactions in a closed-circuit reactor are described, e.g. in JP-A 60/10774, in which a solution containing isocyanate is pumped round, but high yields are obtained only with amine concentrations of 5 to 10%.

In DE-A 32 12 510, a phosgenation reaction takes place in two stages in a closed-circuit reactor in an organic solvent, wherein the first stage is carried out at normal pressure or at pressures up to 10 bar ($10^6$Pa) above atmospheric and at temperatures of 60 to 100° C. with residence times of $\geq 20$ min, and the second stage leading to the isocyanate end product is carried out at the same pressure and temperatures of 120 to 160° C. with residence times of $\geq 10$ min.

DE-B 11 92 641 describes phosgenation reactions in the presence of the isocyanate to be prepared as solvent. When the process is carried out continuously, carbamoyl chloride is formed in the first stage of the reaction with the constant addition of phosgene, and the carbamoyl chloride is split off in a second stage. A disadvantage of said two-stage process is mainly the long reaction time until complete dissolution of the carbamic acid suspension. In continuous operation, the desired isocyanate is obtained as a distillate, i.e. only distillable isocyanates may be produced in this way. Even in batchwise operation, only distillable isocyanates are prepared in the examples.

Phosgenation reactions in the presence of an excess of organic isocyanate are also described in DE-A 22 52 068, wherein carbamoyl chloride is formed in a two-stage process from pre-heated phosgene and pre-heated amine (without solvent) at a pressure above atmospheric (approx. 100 bar) ($10^7$Pa). In the second stage at a lower pressure (approx. 20 bar) ($2.10^6$Pa) and with a further addition of phosgene/isocyanate, carbamoyl chloride undergoes thermal dissociation to the isocyanate. Further work-up takes place at a pressure of 3 bar ($3.10^5$Pa) or at normal pressure. As a result of the four different pressure levels and the two-stage reaction, a very large amount of apparatus is required in said process. Only distillable isocyanates are prepared as examples.

Moreover, a process for the preparation of organic isocyanates is known from DE-A 2 404 773 in which primary amines are mixed with at least 3 mol of phosgene per amino group in the absence of a solvent, the reaction mixture being comminuted at the same time to a mean particle size of 1 to 100 $\mu$m. The suspension of carbamoyl chloride and aminohydrochloride in phosgene obtained is converted to the corresponding isocyanates at temperatures of 100 to 180° C. and at pressures of 14 to 55 bar (1.4 to $5.5.10^6$Pa). A disadvantage of said process is the elaborate and rather unsafe mechanical comminution of the reaction mixture initially produced.

A continuous process for phosgenation at pressures above atmospheric and at temperatures of 110 to 195° C. was described in DE-A 1 468 445. A disadvantage of said process is that a substantial stoichiometric excess of phosgene must be used to obtain high isocyanate yields.

The object of the present invention was, therefore, to provide a process for the preparation of isocyanates which makes it possible to carry out the reaction in a technically simple manner, i.e. in the smallest possible amount of equipment, in high space/time yields.

Surprisingly, it was found that phosgenation reactions may be carried out continuously with a very small amount of technical equipment and in one stage when an isocyanate is used as solvent for phosgene and said mixture is used for phosgenation at room temperature in reactors to be operated continuously, and when the amine is added in the undiluted state or in solution with thorough mixing of the reaction components.

The present invention therefore provides a continuous process for the preparation of isocyanates by reacting appropriate primary amines with phosgene in the presence of an isocyanate as solvent, which is characterised in that the primary amine optionally dissolved in an inert organic solvent is reacted with phosgene which is dissolved in the isocyanate in a quantity of 10 to 60 wt. %, preferably 30 to 50 wt. %, based on the isocyanate/phosgene solution, at temperatures of 60 to 180° C., preferably 80 to 150° C. and at pressures of 1 to 30, preferably 2 to 15, to obtain the corresponding isocyanate, wherein the molar ratio of phosgene to amine used is 4:1 to 1:1, preferably 3:1 to 1.2:1, and the isocyanate used as solvent is solids-free, and has a value for hydrolysable chlorine of less than 2%, preferably less than 1.5.

The primary amines used are preferably primary aromatic amines, particularly those of the diaminodiphenylmethane series or mixtures thereof, optionally with the higher homologues thereof, and toluene diamine and isomer mixtures thereof.

The isocyanate used as solvent for phosgene need not necessarily be the isocyanate to be produced. It is, of course also possible to use other suitable isocyanates as solvent for phosgene.

Inert organic solvents suitable for the primary amines to be used are, in particular, chlorobenzene, o-dichlorobenzene, trichlorobenzene, toluene, hexane, heptane, octane, xylene, biphenyl, ethyl acetate, 1,2-diacetoxyethane, 2-butanone, acetonitrile and sulpholane or mixtures thereof.

If the amine to be used is dissolved in an inert organic solvent, the concentration of the amine in the solvent is usually 10 to 100 wt. %, based on the amine-solvent mixture.

It is important for the process according to the invention that the solvent used for phosgene satisfies a certain specification. In preference, the isocyanate prepared according to the process of the invention is used as solvent, but it must then be worked up in the appropriate way.

The process according to the invention may be carried out in various reactors such as tubular reactors and tower reactors, preferably in tubular reactors.

The process according to the invention may generally be carried out as follows. The primary amine to be used, optionally dissolved in an inert organic solvent, is fed with phosgene dissolved in the isocyanate, both reaction components being mixed together, into a suitable reactor which is operated at the above-mentioned temperatures and pressures. For reasons associated with reactor technology, it may be expedient to mix the two reaction components before they enter the reactor. The mixing of the reaction components may be carried out in conventional mixing equipment such as e.g. dynamic and/or static mixers. The residence times of the reaction components or of the reaction mixture in the reactor and optionally in the mixing equipment is usually 1 to 30 min, preferably 2 to 15 min. The clear solution emerging from the reactor may be depressurised in a suitable apparatus, optionally with additional heating, in order to separate the excess phosgene and the hydrogen chloride formed during the reaction. If the reaction was carried out with an inert organic solvent, a part of the solvent may also be distilled during pressure release and the excess phosgene reused in the reaction after separation of the hydrogen chloride, The remaining inert solvent is then separated from the isocyanate. The inert solvent recovered may be recycled to dissolve the primary amines. After work-up, as mentioned, a part of the isocyanate obtained may be reused for the preparation of the phosgene solution.

The advantages of the process according to the invention to be carried out continuously in one stage lie in particular in the short residence times and in the small amount of apparatus required. As a result of the low pressures required for the process and the small phosgene excess, the process according to the invention may also be operated in a particularly economic manner.

The invention will be explained in more detail on the basis of the examples that follow.

EXAMPLES

The process according to the invention may be carried out in apparatus as shown in the drawing.

The following tests are therefore carried out in apparatus of such kind.

Amine and inert solvent (chlorobenzene) for the amine are conveyed through lines 8 and 9 to the amine/solvent preparation vessel II. The temperature of said vessel is kept at between 30 and 110° C. (at atmospheric pressure), depending on the concentration of the amine solution. In the phosgene/isocyanate preparation vessel I, the amount of the phosgene consumed by the reaction with amine is adjusted by means of a feed via line 7. The temperature in said preparation vessel likewise kept at atmospheric pressure is preferably between 10 and 30° C. The phosgene and amine solutions are conveyed to the mixing unit III at pressures preferably below 10 bar ($10^6$Pa). Downstream of said mixing unit is the tubular reactor IV which is operated preferably at between 80 and 150° C. The residence times in said reactor are dependent on the throughput and reactor volume and are particularly preferably between 1 and 5 minutes. The clear, phosgenated solution emerging from the tubular reactor is conveyed to the distillation unit V. In front of distillation unit V a pressure-maintaining device may be used. In distillation unit V the major part of hydrogen chloride/phosgene and possibly inert solvent are separated at atmospheric pressure and conveyed via line 1 to phosgene work-up unit VIII. In VIII, the inert solvent and hydrogen chloride are removed from the mixture; the purified phosgene is returned to the phosgene/isocyanate preparation vessel I via line 3 and dissolved in the likewise recycled isocyanate. Hydrogen chloride is removed via line 4. Any inert solvent present is fed via line 2 to the inert solvent stream 10, and distilled isocyanate is fed via line 5 to the recycled isocyanate stream 6. The isocyanate which is largely free from phosgene, hydrogen chloride and solvent may then be pumped out of V into another distillation unit VI. There, in addition to the remaining hydrogen chloride/phosgene, the majority of the inert solvent used to dissolve the amine is distilled optionally at preferred temperatures of 160° to 180° C. (optionally under reduced pressure). The inert solvent separated from the isocyanate is passed via line 10 to the solvent work-up unit IX and there dephosgenated, optionally distilled and subsequently returned via line 11 to the amine/solvent preparation vessel. The isocyanate obtained from VI is pumped into the isocyanate preparation vessel VII and the amount of isocyanate that was produced by reacting amine with phosgene is expelled from the circuit. The remainder of the isocyanate is returned via line 6 to the phosgene/isocyanate preparation vessel I.

Examples 1 to 3 were carried out in accordance with DE-B 11 92 641 as comparison tests.

Example 1

200 g of phosgene are introduced into 300 g of a liquid mixture of diphenylmethane diisocyanate isomers (MDI) initially at 25° C. and then at approx. 10° C., and dissolved. 100 g of a diaminodiphenylmethane isomer mixture kept liquid by means of a dropping funnel heated to 70° C. are added dropwise with stirring at below 30° C. whilst a stream of phosgene is introduced continuously into the reaction mixture. A suspension of carbamoyl chloride is formed immediately, which is then heated gradually to 130° C. in the phosgene stream, kept at this temperature for 3.5 hours and phosgenated for a further 45 minutes at 145° C. After nitrogen has been passed through for 30 minutes to expel the phosgene, the reaction product is filtered after cooling to remove small quantities of solid still present.

Example 2

214 g of phosgene are dissolved at 0° C. to 10° C. in 300 g of a liquid MDI-polyisocyanate, composed of 90% binuclear material and 10% higher homologues, and 160 g of a diaminodiphenylmethane isomer/homologue mixture (90% binuclear, 10% higher homologues) kept in the liquid state are added at approx. 25° C. and undergo further treatment as in example 1. After a phosgenation period of 4 hours and 45 minutes, the temperature of the reaction solution was raised to 145° C. and phosgenation continued for another 2 hours until a clear solution was obtained. After nitrogen had been passed through, 485 g of isocyanate were isolated.

Example 3

203 g of phosgene are introduced into 300 g of a liquid mixture of toluene diisocyanate isomers (TDI 80/20, 80 wt. % of 2,4- and 20 wt. % of 2,6-toluene diisocyanate) at 15° to 25° C. and dissolved. 113 g of a melted toluene diamine isomer mixture (80 wt. % of 2,4- and 20 wt. % of 2,6-toluene diamine) are then added at 25° to 30° C. from a heated dropping funnel (110° C.) with stirring. Phosgene continues to be introduced during this period. After heating to 130° C., phosgenation is carried out at this temperature for 2 hours and at 145° C. for a further 2 hours. Further work-up takes place in the manner described in example 2.

Example 4

From a 500 ml preparation vessel provided with heating means, 1.5 l per hour of a 25% solution of a polymer-MDA (diaminodiphenylmethane isomers and higher homologues in chlorobenzene) which has a binuclear content of approx. 50% are combined with 4 l of a 25% phosgene solution (phosgene excess approx. 200% based on the amine) in crude MDI (diphenylmethane diisocyanate isomers and higher homologues; binuclear content between 40 and 50%) in a mixing unit and passed through a tubular reactor with a length of 12.5 m and a reactor volume of 157 ml which is thermostated to 120° C. Installed at the end of the tube is a pressure-maintaining valve which is adjusted to approx. 5 bar ($5.10^5$Pa). The temperature of the amine solution is 30 to 40° C.; the phosgene solution is added at room temperature.

The residence time in the mixing unit and the subsequent tubular reactor is less than 2 minutes. The pressures both on the amine side and the phosgene side are <10 bar ($10^6$Pa). The clear solution emerging from the tubular reactor is depressurised in a 2 l pot for the purpose of dephosgenation, and the majority of the phosgene and hydrogen chloride are removed at temperatures between 130 and 140° C. At these temperatures, a part of the chlorobenzene is already distilled from the reaction mixture and is used as stripping agent, as in the subsequent distillation unit. The MDI/chlorobenzene mixture is pumped from the dephosgenation pot into a thin film evaporator (160° C., 110 to 140 mbar) (1.1 to $1.4 \cdot 10^4$Pa) in order to separate the chlorobenzene and the residual quantities of phosgene and hydrochloric acid.

After chlorobenzene distillation, the amount of isocyanate produced by the reaction of phosgene with polymer-MDA (approx. 470 g/h) is expelled from the circuit and the remainder is returned to the 2.5 l phosgene/MDA preparation vessel and mixed again with phosgene.

The product expelled from the circuit has a viscosity of 150 mPa.s. After the product has been heat treated, a viscosity of 220 mPa.s is obtained. The binuclear content is 43%.

Example 5

In the same way as example 4, a 25% MDA solution in chlorobenzene (throughput: 1.5 l/h), binuclear content MDA approx. 65%) is mixed with a 25% phosgene solution (phosgene excess approx. 200%) in MDI (throughput 3.6 l/h) and passed through a tubular reactor. Downstream of the mixing unit is a 1 m tubular reactor with a volume of 3 ml (room temperature), two 6 m tubes (volume 75 ml each; 110° and 130° C.), a 6 m tube with a volume of 170 ml at 150° C. and a 2 m tube (temperature: 100° C.) which has a volume of 57 ml. The total volume of the tubular reactors is approx. 380 ml, the residence time is approx. 4.5 minutes. The thin film evaporator for removing the residual chlorobenzene is operated at 200° C. and at a pressure of 40 mbar ($4.10^3$Pa). The end product after distillation has a binuclear content of 39%, an NCO value of 31.5% and a viscosity of 180 mPa.s.

Example 6

In the same way as example 4, 110 g of a pure MDA heated to 70° C. (throughput: 0.52 l/h); binuclear content MDA: 66%) are mixed with 1.2 kg of a 40% phosgene solution (phosgene excess approx. 300%) in MDI (room temperature, throughput 4.6 l/h). With a residence time of 2.6 min, the mixture is passed through an 18 m long tubular reactor (volume 226 ml, temperature 150° C.). After dephosgenation at 160° C., the polymer-MDI has a viscosity of 260 mPa.s, after heat treatment a viscosity of 250 mpa.s.

Example 7

In the same way as example 4, 675 g of a 20% solution of toluene diamine solution (TDA 80/20 solution: 80 wt. % of 2,4- and 20 wt. % of 2,6-toluene diamine solution) in chlorobenzene (throughput: 1.5 l/h) are mixed with 2.4 kg of a 25% phosgene solution (phosgene excess approx. 200%) in crude toluene diisocyanate (TDI 80/20: 2,4/2,6 TDI; throughput: 5.1 l/h). The tubular reactor (12 m long and with a volume of 150 ml) was used at temperatures of 135° and 145° C. with a residence time of approx. 2 minutes. After dephosgenation and removal of chlorobenzene, the isocyanate was distilled with a yield of approx. 98.5% and a purity of 99.2% (GC).

Example 8

In the same way as example 4, a TDA without solvent heated to 100 to 105° C. (TDA 80/20, 80 wt. % of 2,4- and 20 wt. % of 2,6-toluene diamine; throughput 330–380 g/h) is mixed with a 40% phosgene solution (phosgene excess 200–250%) in TDI (TDI 80/20; throughput 4880 g/h). With a residence time of 2.6 min, the mixture is passed through an 18 m long tubular reactor (volume 226 ml, temperature 115° C.). After dephosgenation at 160° C., the isocyanate was subsequently distilled.

We claim:

1. A continuous process for the preparation of isocyanates by reacting appropriate primary amines with phosgene in the presence of an isocyanate as solvent, characterised in that the primary amine optionally dissolved in an inert, organic solvent is reacted with phosgene which is dissolved in the isocyanate in a quantity of 10 to 60 wt. % based on the isocyanate/phosgene solution, at temperatures of 60 to 180° C. and at pressures of 1 to 30 bar ($10^5$ to $3.10^6$ Pa) to obtain the corresponding isocyanate, wherein the molar ratio of phosgene to amine used is 4:1 to 1:1 and the isocyanate used as solvent is solids-free and has a value for hydrolysable chlorine of less than 2%.

2. A process according to claim 1, characterised in that the amine used is an amine of the diaminodiphenylmethane series or mixtures thereof, optionally with higher homologues thereof.

3. A process according to claim 1, characterised in that the aromatic amine used is toluene diamine and isomer mixtures thereof.

4. A process according to claim 1, characterised in that the reaction of the amine with phosgene is carried out in a tubular reactor.

* * * * *

UNITED STATES PATENT AND TRADEMARK OFFICE
CERTIFICATE OF CORRECTION

PATENT NO. : 5,925,783
APPLICATION NO. : 08/836294
DATED : July 20, 1999
INVENTOR(S) : Klaus Jost et al.

It is certified that error appears in the above-identified patent and that said Letters Patent is hereby corrected as shown below:

On the title page, item [57] Abstract, change "4 Claims, No Drawings" to "4 Claims, 1 Drawing"

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 5,925,783  
APPLICATION NO. : 08/836294  
DATED : July 20, 1999  
INVENTOR(S) : Klaus Jost et al.

Page 1 of 1

It is certified that error appears in the above-identified patent and that said Letters Patent is hereby corrected as shown below:

Column 3, line 54 under Examples, insert the following drawing

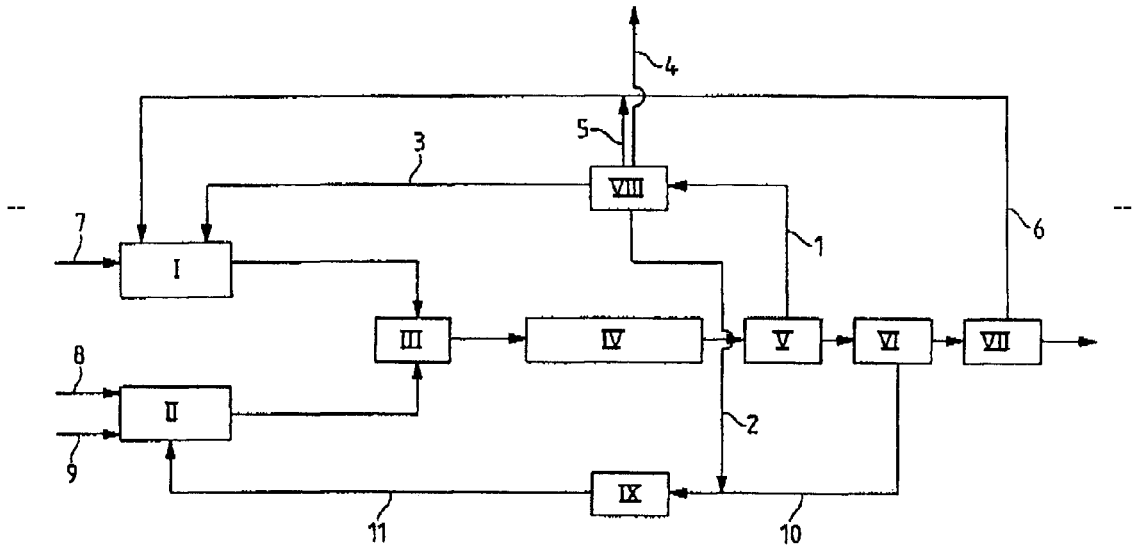

Signed and Sealed this

Third Day of August, 2010

David J. Kappos  
*Director of the United States Patent and Trademark Office*